United States Patent [19]
Izawa

[11] Patent Number: 5,585,274
[45] Date of Patent: Dec. 17, 1996

[54] METHOD FOR MEASURING β-GLUCAN

[75] Inventor: Masayuki Izawa, Yaizu, Japan

[73] Assignee: Sapporo Breweries Limited, Tokyo, Japan

[21] Appl. No.: 394,287

[22] Filed: Feb. 24, 1995

[30] Foreign Application Priority Data

Mar. 10, 1994 [JP] Japan .................................. 6-065423

[51] Int. Cl.$^6$ .................................................. G01N 35/08
[52] U.S. Cl. ........................... 436/52; 422/81; 436/172; 436/815
[58] Field of Search ...................... 422/81, 82; 436/52, 436/53, 91, 145, 172, 815

[56] References Cited

U.S. PATENT DOCUMENTS 4,997,627   3/1991   Bergkuist et al. ..................... 422/81

OTHER PUBLICATIONS

Izawa et al. Proc. Conv.–Inst. Brew. (Asia. Pac. Sect.) 1994 23rd 84–8. "Factors Influencing the determination of . . . ".
Joergensen et al. Proc. Congr.–Eur Brew Conv. 1987, 21st, 361.8. "A specialzed apparatus . . . ".
Mekis et al. J. Inst. Brew., 1987, vol. 93., 396–398. "Modified Fluorimetric Flow–Injection . . . ".
Welch et al. Journal of Cereal Science 9(1989); 35–40 "Kernel (1→3) (1→4)–B–D–Glucan Content of . . . ".
3.11.2 High Molecular Weight Beta–Glucan (Fluorimetric Method), Analytica—EBC (European Brewery Convention), Supplement 1989, E 56/5–7.
Jose M. Sendra et al, Determination of β–Glucan in Wort and Beer by its Binding With Calcofluor, Using a Fluoroimetric Flow–Injection–Analysis (FIA) Method, J. Inst. Brew., Sep.–Oct., 1989, vol. 95, pp. 327–332.
Erika Mekis et al, Modified Fluorimetric Flow–Injection–Analysis (FIA) Method for the Determination of (1–3) (1–4)–B–D–Glucan, J. Inst. Brew., Sep.–Oct., 1987, vol. 93, pp. 396–398.
Paloma Manzanares et al, Selective Determination of β–Glucan of Differing Molecular Size, Using the Calcofluor–Fluorimetric Flow–Injection–Analysis (FIA) Method, J. Inst. Brew., Mar.–Apr., 1991, vol. 97, pp. 101–104.

β–Glucan in Congress Wort by Fluorescence, American Society of Brewing Chemists, Wort–18.
Kevin J. Switala et al, Rapid Determination of β–Glucan in Wort by Flow Injection Analysis, American Society of Brewing Chemists Journal, vol. 47, No. 2, pp. 54–56 (1989).
Sten Aastrup, Application of the Calcofluor Flow Injection Analysis Method for Determination of β–Glucan in Barley, Malt, Wort, and Beer, American Society of Brewing Chemists Journal, vol. 46, No. 3, pp. 76–81 (1988).
Betaglucan Analyzer, Journal of the Institute of Brewing, vol. 93. cover, pp. 1–27 and Appendix 1, 2 and 3.

*Primary Examiner*—James C. Housel
*Assistant Examiner*—Rachel Freed
*Attorney, Agent, or Firm*—Frishauf, Holtz, Goodman, Langer & Chick, P.C.

[57] ABSTRACT

A method for measuring β-(1,3)(1,4)-D-glucan in a sample wherein a reaction solution containing calcofluor and a sample containing β-(1,3)(1,4)-D-glucan are introduced in a reaction zone of a flow injection system and wherein a constant temperature of 0° to 40° C. is maintained at least between a site at which the reactant solution containing calcofluor is mixed with the sample containing β-(1,3)(1, 4)-D-glucan, and a detector. When the amount of sample injected into the system is between 0.002 ml and 0.1 ml, the relationship between the void volume in the reaction zone and the amount of sample introduced into the system is determined as follows: when the void volume is less than 0.4 ml: 0.03×(void volume (ml))+0.0018≦amount of sample (ml)≦0.066×(void volume (ml))+0.0018; when the void volume is 0.4 ml or more: 0.01×(void volume (ml))+0.0098≦amount of sample (ml)≦0.026×(void volume (ml))+0.00178. The present invention results in an accurate and reproducible measurement of the β-(1,3)(1,4)-D-glucan content in a sample, even if saccharides and ethanol are present. Therefore, using the method of the present invention, it is possible to objectively compare and evaluate the β-(1,3)(1,4)-D-glucan contents in various samples, such as cereals, malt extract, wort, beer, etc.

8 Claims, 1 Drawing Sheet

METHOD FOR MEASURING β-GLUCAN

FIELD OF THE INVENTION

The present invention relates to a method for measuring β-(1,3)(1,4)-D-glucan (hereinafter referred to as β-glucan) and, more precisely, to a method for measuring β-glucan which is in various cereals such as barley, etc. and in malt, wort, beer, etc.

BACKGROUND OF THE INVENTION

Calcofluor which is represented by the following structural formula is a fluorescent compound which specifically bonds to β-glucan to have an increased degree of fluorescent intensity due to the bonding. Jørgensen et al. of Carlsberg Co. in Denmark have reported flow injection using this compound (see Carlsberg Res. Commun., Vol. 53, pp. 277–285, 1988; Analytica-EBC, 3.11.2.).

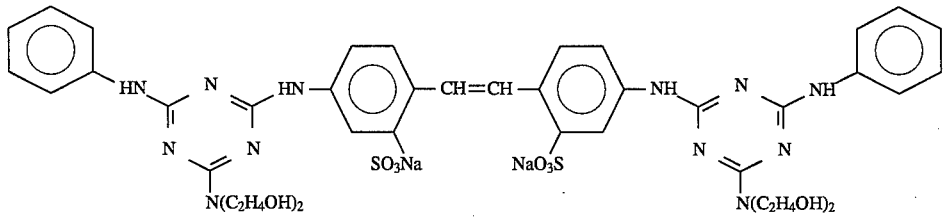

Some other researchers have also reported flow injection using calcofluor on the basis of the same principle (see Journal of the Institute of Brewing, Vol. 95 p. 327, 1989; Journal of the Institute of Brewing, Vol. 93, p. 396, 1987). Recently, commercial flow injection systems using calcofluor have been sold in the market by Tecator Co. in Sweden and by Fiatron Co. in USA (see Journal of the American Society of Brewing Chemists, Vol. 93, p. 396, 1087).

These are all applied or modified systems from the system shown in FIG. 1 or FIG. 2, in which a flow of a sample or a solution containing a sample is mixed with a flow of a reactant solution prepared by dissolving from 8 to 35 mg/liter of calcofluor in a tris or glycine buffer having pH of from 8 to 10, by which calcofluor is bonded to β-glucan in the sample, using a suitable tube, and the increase in the fluorescent intensity of the thus-bonded compound is measured using a fluorophotometer.

To determine the β-glucan content in a sample such as wort, beer, etc. by these methods, is used, as a reference sample, a solution containing a known concentration of pure β-glucan extracted from barley.

However, it has been experienced that the conditions for the measurement by the conventional flow injection methods using calcofluor, that have heretofore been reported, such as the amount of the sample to be injected, the length and the void volume in the mixing tube, the flow rates, the pH value and the calcofluor concentration of the reactant solution, etc. vary, resulting in that the value of the β-glucan content in the same sample obtained by the measurement varies. Particularly in the reports that have heretofore been made, the temperature condition for the measurement is not specifically defined and the measurement has generally been conducted at any desired room temperature. As a result, it is recognized that the value of the β-glucan content in a sample, such as wort, beer, etc., that is measured by any of the conventional flow injection methods varies, depending on the temperature condition for the measurement.

The increase in the fluorescent intensity resulting from the bonding of calcofluor and β-glucan varies, depending on the change in temperature, and the degree of the variation differs between a high-molecular β-glucan having a molecular weight of 100,000 or more in the reference sample and a low-molecular β-glucan having a molecular weight of not more than 100,000, which should be in beer, wort, etc. in a small amount. It has become recognized that the increase in the fluorescent intensity resulting from the reaction of such a low-molecular β-glucan and calcofluor is higher than that from the reaction of a high-molecular β-glucan and calcofluor, whenever measured at lower temperatures.

For these reasons, the value of the β-glucan content in a sample, such as beer, wort, etc., containing such a low-molecular β-glucan is higher, whenever measured at lower temperatures. In general, wort contains various saccharide components, while beer contains ethanol in addition to saccharides. Also it has become recognized that such additional components have an influence on the values to be measured by the conventional flow injection methods using calcofluor.

It is obvious that such causes errors in the measurement of β-glucan to be in extracts of barley, wort, beer, etc. Accordingly, it is effective to control systems which are not influenced by temperatures, saccharides, ethanol, etc. and also to settle the conditions for measurement by such systems so as to improve the accuracy in the measurement. Thus, the development of such systems is desired.

SUMMARY OF THE INVENTION

The object of the present invention is to improve the accuracy in the measurement of β-glucan by flow injection using calcofluor and also the reproducibility of the measurement. The first means for attaining the object according to the present invention is to carry out the measurement, though having heretofore been carried out at any desired room temperature, at the same determined temperature in some parts of the system for flow injection, but most preferably throughout the system, by which the variation in the measured value to be caused by the change in temperatures is prevented. The second means is to reduce the influence by the other components than the intended β-glucan, such as saccharides, ethanol, etc., in a sample, while controlling the suitable conditions under which objective values can be obtained for different samples.

Specifically, the present invention provides a method for measuring β-glucan in a sample by a flow injection system using calcofluor, in which the reaction zone in the system between the site, at which a reactant solution containing calcofluor is mixed with the sample containing β-glucan, and a detector is kept at a constant temperature selected from a temperature of from 0° to 40° C. It also provides a method for measuring β-(1,3)(1,4)-D-glucan in a sample by a flow injection system using calcofluor, in which the amount of the sample to be injected into the system is within the range between 0.002 ml and 0.1 ml and satisfies the following condition, when the void volume in the reaction zone is less than 0.4 ml;

0.03×[void volume (ml)]+0.0018≦amount of sample injected (ml)≦0.066×[void volume (ml)]+0.0018 while satisfying the following condition, when the void volume in the same zone is 0.4 ml or more;

0.01×[void volume (ml)]+0.0098≦amount of sample injected (ml)≦0.026×[void volume (ml)]+0.00178.

In these drawings, 1 is a calcofluor-containing reactant solution, 2 is a pump, 3 is a sample injector, 4 is a reaction zone, 5 is an integrator, 6 is a fluorophotometer, 7 is a waste liquid, and 8 is a buffer.

DETAILED DESCRIPTION OF THE INVENTION

Figure 1:
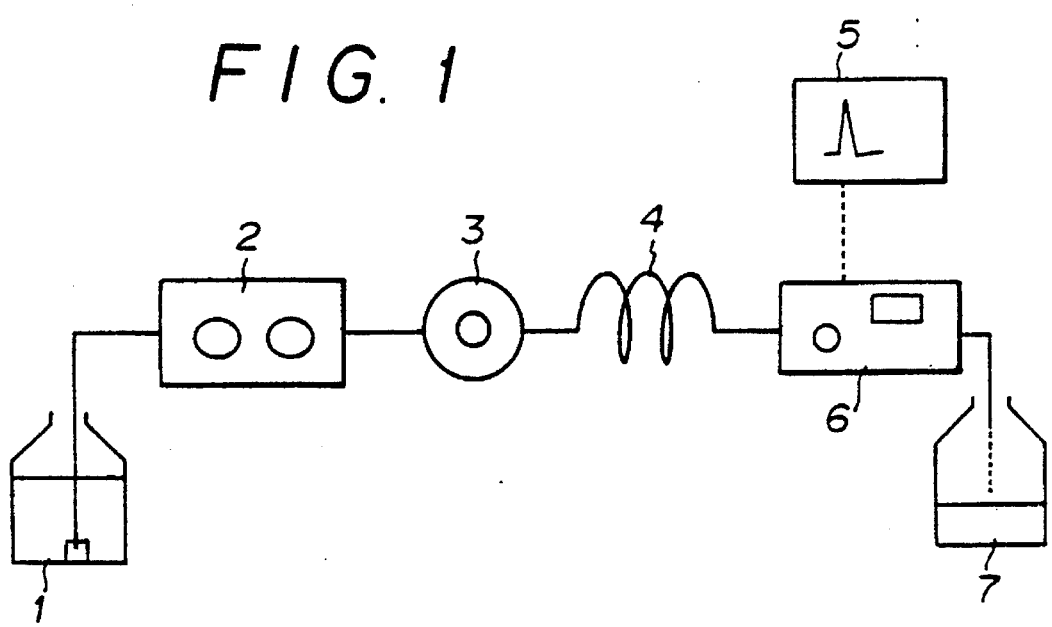
FIG. 1 shows one example of a system for measuring the β-glucan content in a sample by flow injection using calcofluor.
Figure 2:
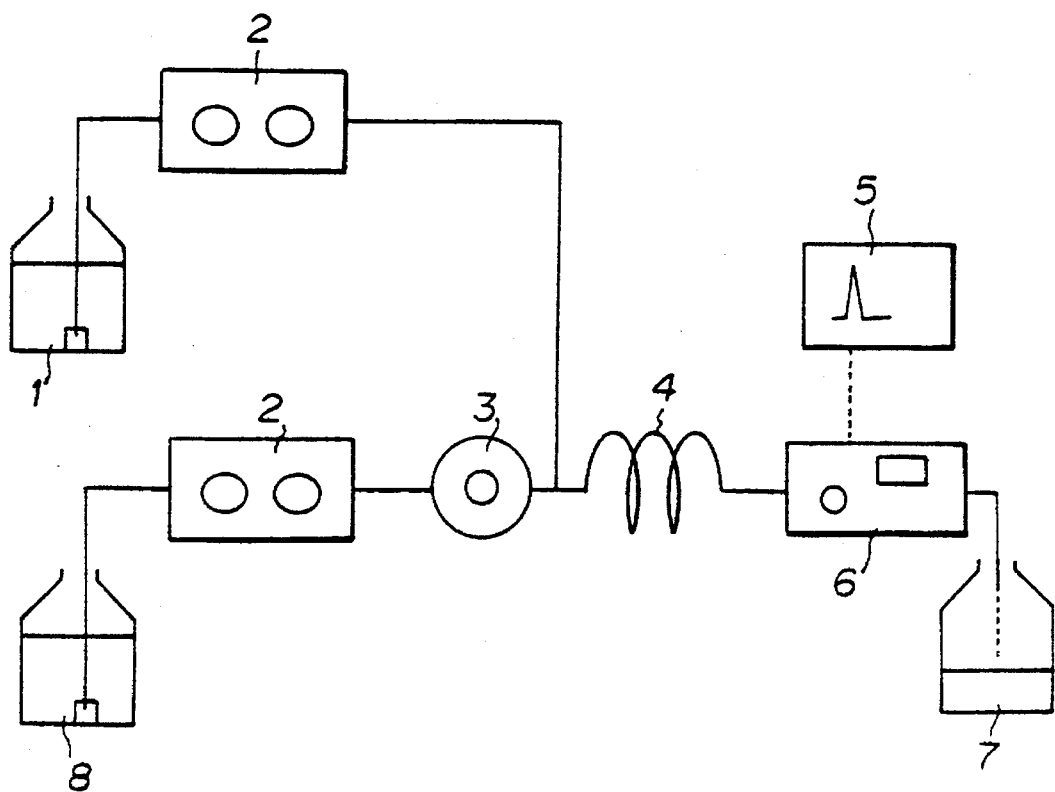
FIG. 2 shows another example of a system for measuring the β-glucan content in a sample by flow injection using calcofluor.

It is possible to directly apply the method of the present invention to the conventional systems such as those shown in FIG. 1 and FIG. 2.

The most important area in the system where the temperature for the measurement shall be kept constant according to the present invention comprises the reaction zone and the mixing zone from the site at which the sample is injected into the system to the detector. Since the substantial bonding of calcofluor to β-glucan is effected in this area, the temperature in this area is kept constant whereby the variation in the measured value caused by the change in the ambient temperature can be reduced almost satisfactorily.

More effectively, the calcofluor-containing reactant solution and the container containing it are kept at the same temperature. If the reaction zone in the system is short, there will be a probability that the sample reacted cannot reach the intended temperature before it reaches the detector. In such a case, it is considered that the temperature of the reactant solution must be previously made the same as the temperature in the reaction zone.

More desirably, the detector and the reaction zone are kept at the same temperature. The reason is because of the probability that the temperature of the sample will vary in the inside of the detector before the sample reaches the cell of the detector at which the substantial measurement of the sample is conducted. To most effectively inhibit the influence by the variation in temperatures, the entire system including not only the above-mentioned area but also the pump and the sample injector is kept at the determined constant temperature.

However, too high temperatures for the measurement are undesirable as inhibiting the bonding of calcofluor to β-glucan. In general, the temperature is fixed at a temperature selected from 0° C. to 40° C. for practicable performance. Where the entire system is kept at a constant temperature, the temperature is desirably selected from 15° C. to 30° C. or so.

Of various conditions for the measurement of β-glucan in a sample by flow injection using calcofluor, the amount of the sample to be injected and the void volume in the reaction zone in the system have the most significant relation to the influence by saccharides and ethanol in the sample on the measured value. The greater the amount of the sample injected, the lower the value of β-glucan measured in the sample containing saccharides and ethanol than the value of the same in the sample not containing them. On the contrary, however, if the amount of the sample injected is less than a certain limit, the value of β-glucan measured in the sample containing saccharides and ethanol is larger than the value of the same in a sample not containing them.

The presence of the critical limit for the amount of the sample injected, at which the influence by saccharides and ethanol in the sample on the value of β-glucan measured changes in such a way that the value of β-glucan measured in the sample containing saccharides and ethanol is made higher than that measured in a sample not containing these, has been found. However, the critical limit for the amount of the sample injected varies, depending on the void volume in the reaction zone. Therefore, there should be a particular amount of the sample injected, which is not influenced so much by saccharides and ethanol in the sample relative to a particular value of the void volume in the reaction zone. However, these are additionally influenced by the other conditions for the measurement in some degree, while varying also in some degree depending on the kind and the content of saccharides and ethanol to be in the sample. Therefore, it is suitable to fix the following conditions for the method of the present invention.

The amount of the sample injected into the system is within the range between 0.002 ml and 0.1 ml and satisfies the following condition, when the void volume in the reaction zone is less than 0.4 ml;

0.03×[void volume (ml)]+0.0018≦amount of sample injected (ml)≦0.066×[void volume (ml)]+0.0018 while satisfying the following condition, when the void volume in the same zone is 0.4 ml or more;

0.01×[void volume (ml)]+0.0098≦amount of sample injected (ml)≦0.026×[void volume (ml)]+0.00178.

These conditions are described in detail. It is preferred that the amount of the sample injected is from 0.006 to 0.014 ml when the void volume in the reaction zone is from 0.1 to 0.2 ml; the amount is from 0.008 to 0.017 ml when the void volume is from 0.2 to 0.25 ml; the amount is from 0.011 to 0.019 ml when the void volume is from 0.25 to 0.3 ml; the amount is from 0.012 to 0.025 ml when the void volume is from 0.3 to 0.4 ml; the amount is from 0.013 to 0.03 ml when the void volume is from 0.4 to 0.6 ml; the amount is from 0.015 to 0.035 ml when the void volume is from 0.6 to 0.8 ml; the amount is from 0.02 to 0.04 ml when the void volume is from 0.8 to 1.0 ml; the amount is from 0.025 to 0.05 ml when the void volume is from 1.0 to 1.5 ml; and the amount is from 0.03 to 0.06 ml when the void volume is from 1.5 to 2.0 ml.

When the measurement is conducted under the thus-fixed conditions according to the present invention, it is possible to obtain a more objective value of β-glucan measured in the absence of the influence by saccharides and ethanol on the value measured, as compared with the conventional method of measuring β-glucan by flow injection using calcofluor.

According to the method of the present invention, accurate and reproducible measurement of the β-glucan content in a sample, even though containing saccharides and ethanol, is possible without being influenced by such saccharides and ethanol in the sample. Therefore, using the method of the present invention, it is possible to objectively compare and evaluate the β-glucan contents in various samples, such as various cereals, malt extract, wort, beer, etc.

While the invention has been described in detail and with reference to specific embodiments thereof, it will be apparent to one skilled in the art that various changes and modifications can be made therein without departing from the spirit and scope thereof.

The present invention will be described in more detail by means of the following examples, which, however, are not intended to restrict the scope of the present invention.

Example 1

The system shown in FIG. 1 was used at a pre-determined constant room temperature. As the reactant solution, used was 0.1M glycine-NaOH buffer (pH 9) containing 15 mg/liter of calcofluor and 10 mg/liter of Triton X-100. Its flow rate was 3 ml/min. In the fluorophotometer used, the excited wavelength was 360 nm and the fluorescent wavelength was 420 nm. As the reaction zone, used was a Teflon (Trade name) tube having an inner diameter of 0.5 mm and a length of 4 m. The amount of the sample injected was 0.02 ml. The temperature of the reaction zone was controlled at 20° C., using a thermostat.

As the reference solutions, used were solutions that had been prepared by dissolving 30 mg/liter, 50 mg/liter, 75 mg/liter, 100 mg/liter, 150 mg/liter, 200 mg/liter, 250 mg/liter and 300 mg/liter of pure β-glucan extract from barley (produced by Sigma Co.). in distilled water. From the heights of the peaks of these reference solutions, a calibration curve was prepared.

On the other hand, wort A or beer A was used as the sample, of which the height of the peak was measured. On the basis of the above-mentioned calibration curve, the β-glucan content in the sample was determined. The results are shown in Table 1 below.

Example 2

The sample of wort A or beer- A was measured, using the same system under the same conditions as in Example 1, except that the temperature of the reactant solution and its container was controlled at 20° C. using a thermostat. The height of the peak of the sample was measured, from which the β-glucan content in the sample was determined on the basis of the calibration curve that had been prepared from the same reference solutions as those in Example 1. The results are shown in Table 1.

Example 3

The sample of wort A or beer A was measured, using the same system under the same conditions as in Example 1, except that the temperature of the entire system was controlled at 20° C. using a thermostat. The height of the peak of the sample was measured, from which the β-glucan content in the sample was determined on the basis of the calibration curve that had been prepared from the same reference solutions as those in Example 1. The results are shown in Table 1.

Example 4

The sample of wort A or beer A was measured, using the same system under the same conditions as in Example 1, except that the temperature of the entire system was controlled at 25° C. using a thermostat. The height of the peak of the sample was measured, from which the β-glucan content in the sample was determined on the basis of the calibration curve that had been prepared from the same reference solutions as those in Example 1. The results are shown in Table 1.

TABLE 1

| Variation in β-Glucan Content (ppm) in Samples under Various Measuring Temperatures | | | | | | |
|---|---|---|---|---|---|---|
| Measuring Temperature | 18° C. | | 22° C. | | 25° C. | |
| Sample | wortA | beerA | wortA | beerA | wortA | beerA |
| Example 1 Constant temperature of 20° C. in the reaction zone | 92 | 154 | 89 | 147 | 87 | 144 |
| Example 2 Constant temperature of 20° C. in the reaction zone and the reactant solution | 91 | 151 | 90 | 148 | 89 | 146 |
| Example 3 Constant temperature of 20° C. in the entire system | 90 | 148 | 90 | 148 | 90 | 147 |
| Example 4 Constant temperature of 25° C. in the entire system | 84 | 138 | 84 | 137 | 84 | 137 |
| Comparative Example 1 Varying room temperature in the entire system | 98 | 163 | 88 | 145 | 83 | 138 |

Example 5

The same system as in Example 3 was employed, except that a Teflon (Trade name) tube having an inner diameter of 0.5 mm and a length of 1 m was fixed into the reaction zone and that the amount of the sample injected was 0.01 ml. Three samples were measured herein. Sample No. 1 was an aqueous solution containing a low-molecular β-glucan that had been prepared by dissolving pure β-glucan from barley in 0.1N sulfuric acid, hydrolyzing it in a boiling bath for one hour and then neutralizing it with sodium hydroxide (hereinafter referred to as a low-molecular β-glucan); sample No. 2 was an aqueous solution containing the low-molecular β-glucan and 5% ethanol; and sample No. 3 was an aqueous solution containing the low-molecular β-glucan and 10% maltose. The height of the peak of each sample was measured, from which the β-glucan content in each sample was determined on the basis of the calibration curve that had been prepared from the same reference solutions as those in Example 1. The results are shown in Table 2 along with those in Example 3.

Comparative Example 1

The sample of wort A or beer A was measured, using the same system under the same conditions as in Example 1, except that the temperature of the entire system including the reaction zone was not specifically controlled but was at varying room temperature. The height of the peak of the sample was measured, from which the β-glucan content in the sample was determined on the basis of the calibration curve that had been prepared from the same reference solutions as those in Example 1. The results are shown in Table 1.

Comparative Example 2

Using the same system as in Example 3, the following three samples were measured under the same conditions as in Example 3, except that the amount of each sample injected was 0.01 ml. Sample No. 1 was an aqueous solution containing the low-molecular β-glucan (see Example 5); sample No. 2 was an aqueous solution containing the low-molecular β-glucan and 5% ethanol; and sample No. 3 was an aqueous solution containing the low-molecular β-glucan and 10% maltose. The height of the peak of each sample was measured, from which the β-glucan content in each sample was determined on the basis of the calibration curve that had been prepared from the same reference solutions as those in Example 1. The results are shown in Table 2.

Comparative Example 3

Using the same system as in Example 5, the following three samples were measured under the same conditions as in Example 3, except that the amount of each sample injected was 0.025 ml. Sample No. 1 was an aqueous solution containing the low-molecular β-glucan (see Example 5); sample No. 2 was an aqueous solution containing the low-molecular β-glucan and 5% ethanol; and sample No. 3 was an aqueous solution containing the low-molecular β-glucan and 10% maltose. The height of the peak of each sample was measured, from which the β-glucan content in each sample was determined on the basis of the calibration curve that had been prepared from the same reference solutions as those in Example 1. The results are shown in Table 2.

TABLE 2

Influence by saccharide and ethanol in sample on the measured value (ppm)

|  | Example 3 | Example 5 | Comparative Example 2 | Comparative Example 3 |
|---|---|---|---|---|
| Void volume in reaction zone (ml) | 0.785 | 0.196 | 0.785 | 0.785 |
| Amount of sample injected (ml) | 0.02 | 0.01 | 0.01 | 0.025 |
| Low-molecular β-glucan | 69 | 71 | 74 | 66 |
| Low-molecular β-glucan + ethanol | 69 | 70 | 78 | 60 |
| Low-molecular β-glucan + maltose | 70 | 72 | 83 | 61 |

As is obvious from the results in Table 1 above, it was confirmed that the variation in the value of the β-glucan content measured was inhibited by partly or entirely controlling the temperature of the system at a pre-determined constant temperature in Examples 1 to 4, whilst the value of the β-glucan content measured varied according to the variation in the room temperature in Comparative Example 1.

The influence by maltose (saccharide) and ethanol on the measurement of the low-molecular β-glucan content in samples was investigated and the test results are shown in Table 2, from which it was confirmed that the measured values were not substantially influenced by the saccharide and ethanol in the examples of the present invention where the amount of the sample injected was suitably defined relative to the void volume in the reaction zone, whilst the measured values were significantly influenced by these in the comparative examples where the amount of the sample injected did not satisfy the conditions of the present invention.

What is claimed is:

1. A method for measuring β-(1,3)(1,4)-D-glucan in a sample by flow injection system comprising introducing (i) a reactant solution containing calcofluor and (ii) a sample containing β-(1,3)(1,4)-D-glucan, in a reaction zone of the flow injection system and maintaining a constant temperature of 0° to 40° C. at least between a site at which the reactant solution containing calcofluor is mixed with the sample containing β-(1,3)(1,4)-D-glucan, and including a detector.

2. The method for measuring β-(1,3)(1,4)-D-glucan as claimed in claim 1, in which the reactant solution is introduced into the reaction zone from a container containing the reactant solution, and the reactant solution and the container containing the reactant solution are both maintained at said constant temperature of 0° to 40° C.

3. The method for measuring β-(1,3)(1,4)-D-glucan as claimed in claim 1, in which the entire flow injection system including a pump for pumping the reactant solution from a container through a pump line, and a sample injector, is maintained at said constant temperature of 0° to 40° C.

4. The method for measuring β-(1,3)(1,4)-D-glucan as claimed in any one of claims 1 to 3, in which the sample is introduced by injection and the amount of the sample injected into the system is 0.002 ml to 0.1 ml and wherein the following conditions are satisfied:

when a void volume in the reaction zone is less than 0.4 ml:

0.03×(void volume (ml))+0.0018≦amount of sample (ml)≦0.066×(void volume (ml))+0.0018, when the void volume in said reaction zone is 0.4 ml or more:

0.01×(void volume (ml))+0.0098≦amount of sample (ml)≦0.026×(void volume (ml))+0.00178.

5. A method for measuring β-(1,3)(1,4)-D-glucan in a sample by a flow injection system comprising injecting (i) a sample containing β-(1,3)(1,4)-D-glucan, and (ii) calcofluor in a reaction zone, and maintaining an amount of the sample introduced into the flow injection system between 0.002 ml and 0.1 ml and wherein the following conditions are satisfied:

when a void volume in the reaction zone is less than 0.4 ml:

0.03×(void volume (ml))+0.0018≦amount of sample (ml)≦0.066×(void volume (ml))+0.0018, when the void volume in said reaction zone is 0.4 ml or more:

$0.01\times(\text{void volume (ml)})+0.0098 \leq$ amount of sample (ml) $\leq 0.026\times(\text{void volume (ml)})+0.00178$.

6. The method for measuring β-(1,3)(1,4)-D-glucan as claimed in claim 1, wherein the β-(1,3)(1,4)-D-glucan is a β-(1,3)(1,4)-D-glucan which is contained in a cereal, malt, wort or beer.

7. The method for measuring β-(1,3)(1,4)-D-glucan as claimed in claim 1, wherein the constant temperature is maintained at a temperature of 15° to 30° C.

8. The method for measuring β-(1,3)(1,4)-D-glucan as claimed in claim 7, wherein the sample is injected into the reaction zone in an amount which corresponds with the following void volumes in the reaction zone:

the amount of the sample is from 0.006 to 0.014 ml when the void volume in the reaction zone is from 0.1 to 0.2 ml;

the amount of the sample is from 0.008 to 0.017 ml when the void volume is from 0.2 to 0.25 ml;

the amount of the sample is from 0.011 to 0.019 ml when the void volume is from 0.25 to 0.3 ml;

the amount of the sample is from 0.012 to 0.025 ml when the void volume is from 0.3 to 0.4 ml;

the amount of the sample is from 0.013 to 0.03 ml when the void volume is from 0.4 to 0.6 ml;

the amount of the sample is from 0.015 to 0.035 ml when the void volume is from 0.6 to 0.8 ml;

the amount of the sample is from 0.02 to 0.04 ml when the void volume is from 0.8 to 1.0 ml;

the amount of the sample is from 0.025 to 0.05 ml when the void volume is from 1.0 to 1.5 ml; and the amount of the sample is from 0.03 to 0.06 ml when the void volume is from 1.5 to 2.0 ml.

* * * * *